(12) United States Patent
Kintzig

(10) Patent No.: US 6,176,119 B1
(45) Date of Patent: Jan. 23, 2001

(54) ANALYTICAL SYSTEM FOR SAMPLE LIQUIDS

(75) Inventor: Hans Kintzig, Tiefenthal (DE)

(73) Assignee: Roche Diagnostics GmbH (DE)

( * ) Notice: Under 35 U.S.C. 154(b), the term of this patent shall be extended for 0 days.

(21) Appl. No.: 09/210,329

(22) Filed: Dec. 11, 1998

(30) Foreign Application Priority Data

Dec. 13, 1997 (DE) .............................................. 197 55 529

(51) Int. Cl.$^7$ .......................... G01N 21/47; G01N 01/28; G01N 35/04; G01N 33/00

(52) U.S. Cl. ...................... 73/53.01; 73/53.04; 73/865.6; 422/63; 422/58

(58) Field of Search ................................ 73/53.01, 53.04, 73/53.06, 54.07, 54.21, 865.6, 866.1, 64.56; 422/63–65, 57–58

(56) References Cited

U.S. PATENT DOCUMENTS

| | | | |
|---|---|---|---|
| 2,379,835 | * | 7/1945 | Sisler ........................................ 73/63 |
| 2,486,080 | * | 10/1949 | Turner et al. ............................. 73/64 |
| 2,615,329 | * | 10/1952 | Witham .................................... 73/63 |
| 3,093,997 | * | 6/1963 | Uhrmacher ............................... 73/54 |
| 3,266,298 | * | 8/1966 | Whitehead et al. ...................... 73/53 |
| 4,118,280 | | 10/1978 | Charles et al. ......................... 195/127 |
| 4,356,722 | * | 11/1982 | Bunce et al. ............................. 73/53 |
| 4,406,159 | * | 9/1983 | Yanishevsky ............................. 73/63 |
| 4,554,821 | * | 11/1985 | Kiesewetter et al. .................... 73/55 |
| 4,566,314 | * | 1/1986 | Thurston .................................. 73/55 |
| 4,797,256 | | 1/1989 | Watlington, IV ....................... 422/58 |
| 4,948,737 | | 8/1990 | Quenin et al. .......................... 436/46 |
| 5,314,661 | | 5/1994 | Mulqueen ............................... 422/57 |
| 5,325,709 | * | 7/1994 | Lee ....................................... 73/61.43 |
| 5,447,690 | | 9/1995 | Sugaya .................................. 422/64 |
| 5,686,047 | | 11/1997 | Augstein ................................ 422/65 |
| 5,690,892 | | 11/1997 | Babler et al. .......................... 422/63 |
| 5,710,371 | * | 1/1998 | Gzernectri et al. ................. 73/53.01 |

FOREIGN PATENT DOCUMENTS

| | | | |
|---|---|---|---|
| 31 51 291 A1 | 8/1982 | (DE) | ............................... G01N/33/48 |
| 0 377 503 A2 | 7/1990 | (DE) | ................................. B01L/9/06 |

(List continued on next page.)

*Primary Examiner*—Hezron Williams
*Assistant Examiner*—David Wiggins
(74) *Attorney, Agent, or Firm*—Richard T. Knauer.; Roche Diagnostics Corporation

(57) ABSTRACT

The invention concerns a system for the analysis of sample liquids, comprising:

a) test elements comprising an edge profile;

b) a moisture-impermeable, tightly sealable storage container for at least two test elements comprising a guide element, a spacer between the guide element and the first test element to be withdrawn, and a transport device for test elements; and c) a measuring instrument that is independent of a power supply network and can be held with one hand, the instrument comprising a guide groove for test elements, an opposing guide groove for the guide element of the storage container, and a holding device for test elements.

The invention also concerns a method for the determination of an analyte in a sample liquid with the aid of a measuring instrument, comprising:

a) removing a test element from an open storage container with the aid of the measuring instrument;

b) contacting a sample application zone of the test element located in the instrument with a sample liquid which is automatically transported into a detection zone so that the sample liquid there reacts characteristically and detectably with the components of the test zone;

c) detecting and displaying the reaction result with the aid of the measuring instrument; and d) removing the used test element from the measuring instrument after the analysis.

15 Claims, 5 Drawing Sheets

FOREIGN PATENT DOCUMENTS

| | | | |
|---|---|---|---|
| 0 487 068 A1 | 5/1992 | (DE) | G01N/33/52 |
| 0 513 618 A3 | 11/1992 | (DE) | G01N/35/06 |
| 0 271 854 B1 | 3/1993 | (DE) | G01N/33/52 |
| 42 34 553 A 1 | 4/1993 | (DE) | A61B/5/14 |
| 42 05 805 A 1 | 9/1993 | (DE) | B65D/83/08 |
| 0 618 443 A1 | 10/1994 | (DE) | G01N/21/86 |
| 195 23 049 A1 | 1/1997 | (DE) | G01N/31/22 |
| 196 29 656 A1 | 1/1998 | (DE) | G01N/33/52 |
| 196 29 657 A1 | 1/1998 | (DE) | G01N/33/52 |
| 0 215 419 A2 | 3/1987 | (EP) | G01N/1/00 |
| 0 794 424 A1 | 9/1997 | (EP) | G01N/21/47 |
| WO 92/17768 | 10/1992 | (WO) | G01N/21/77 |

\* cited by examiner

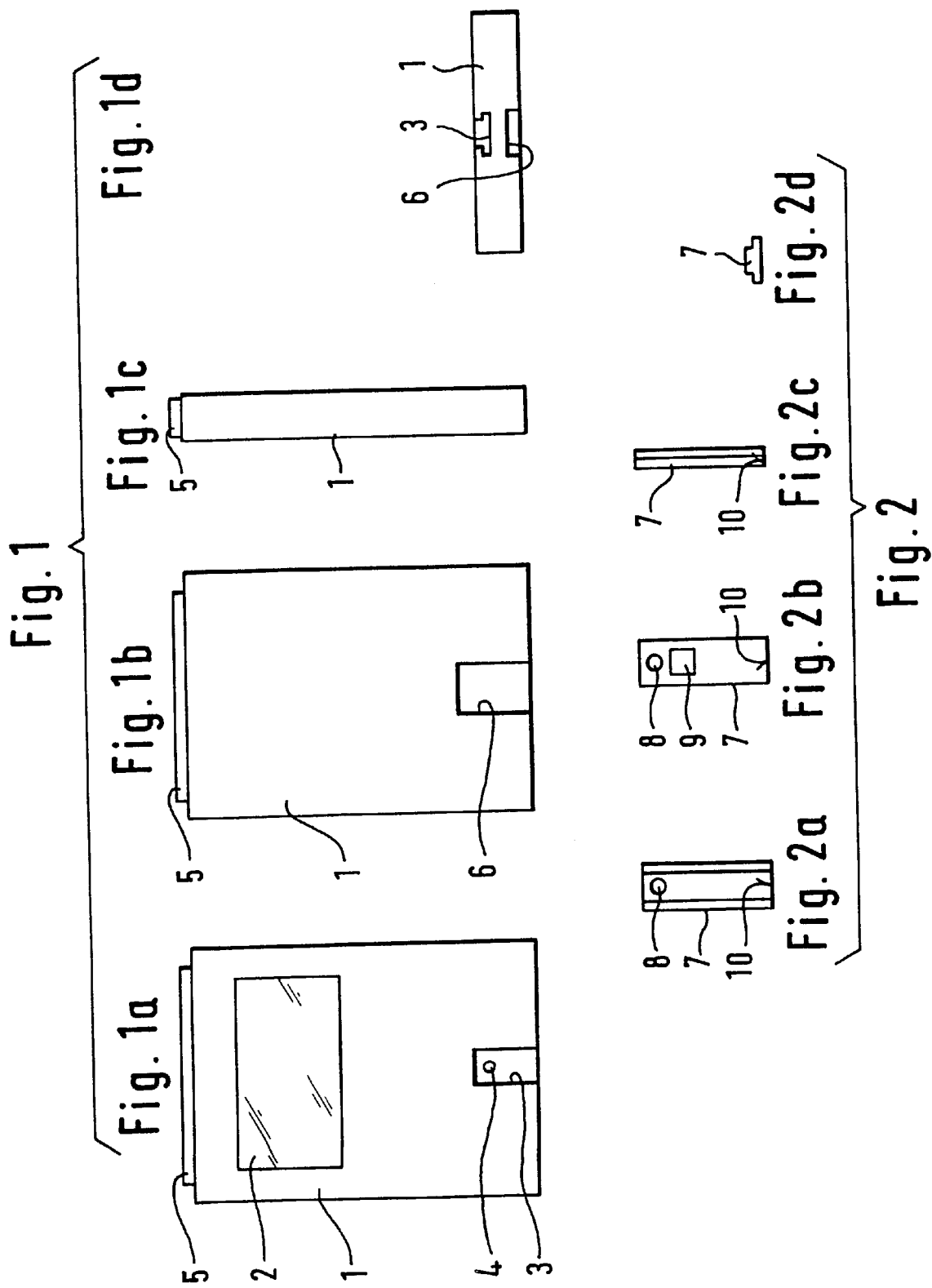

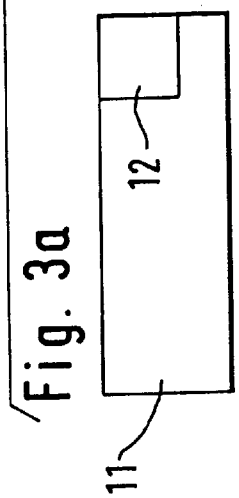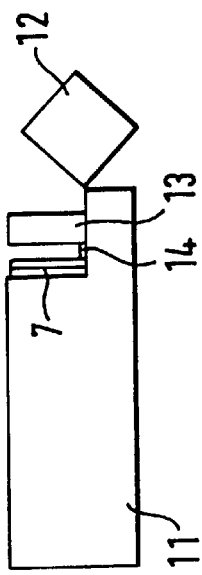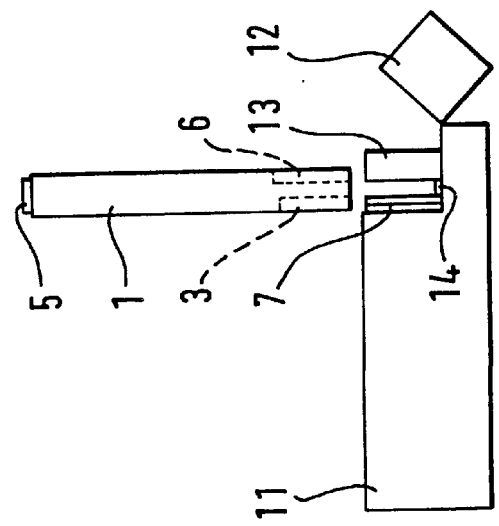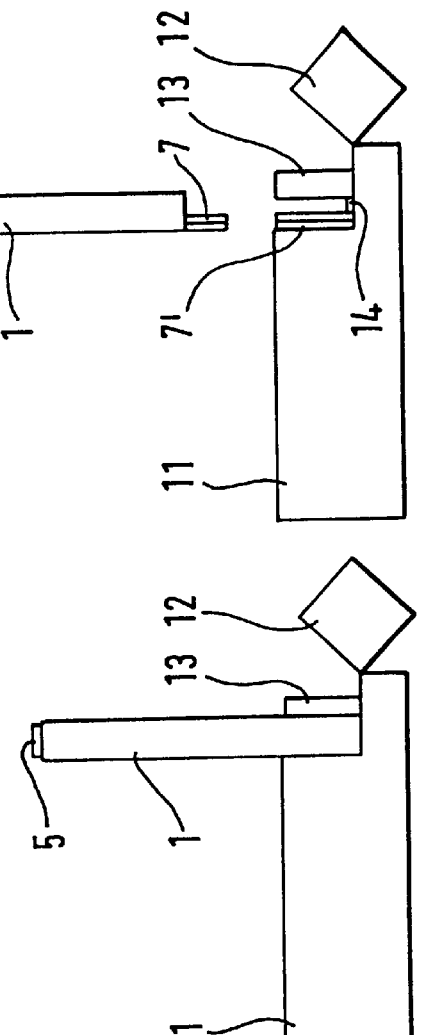

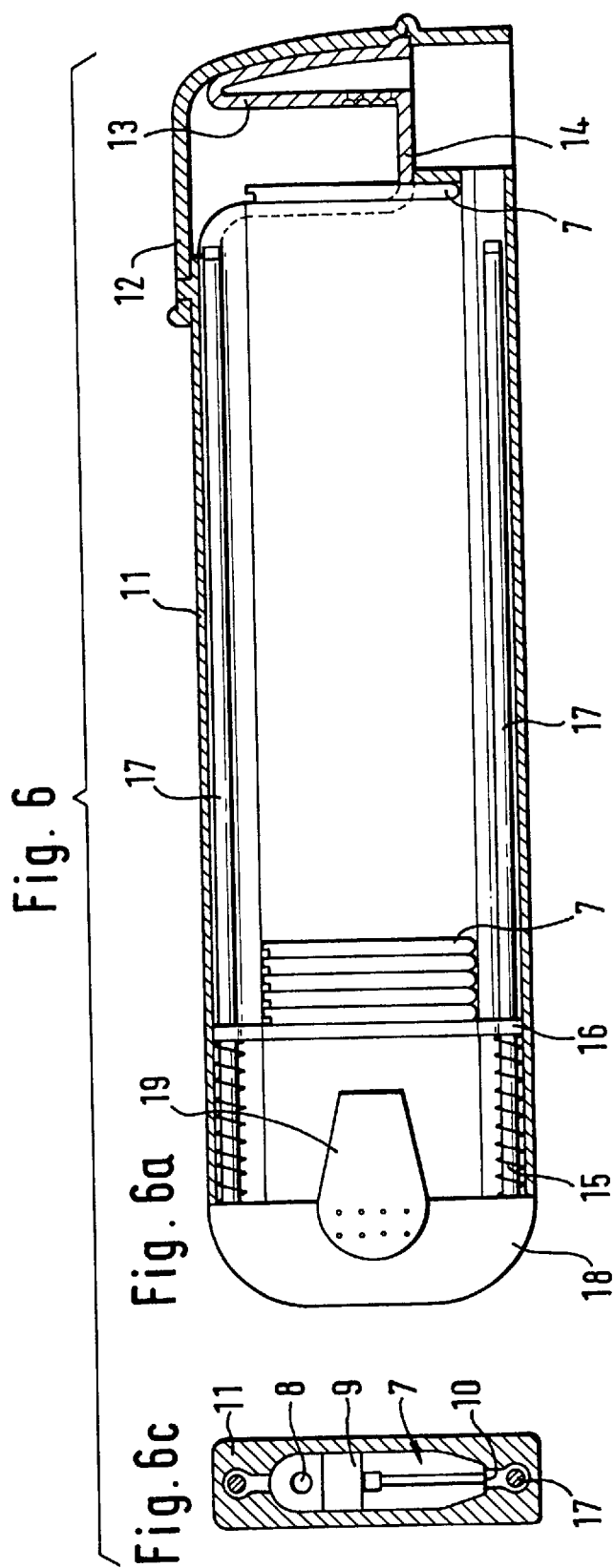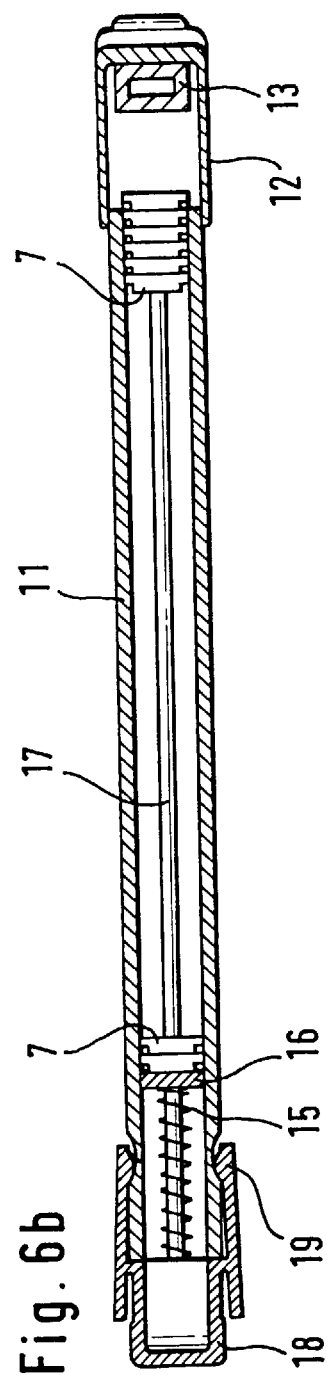

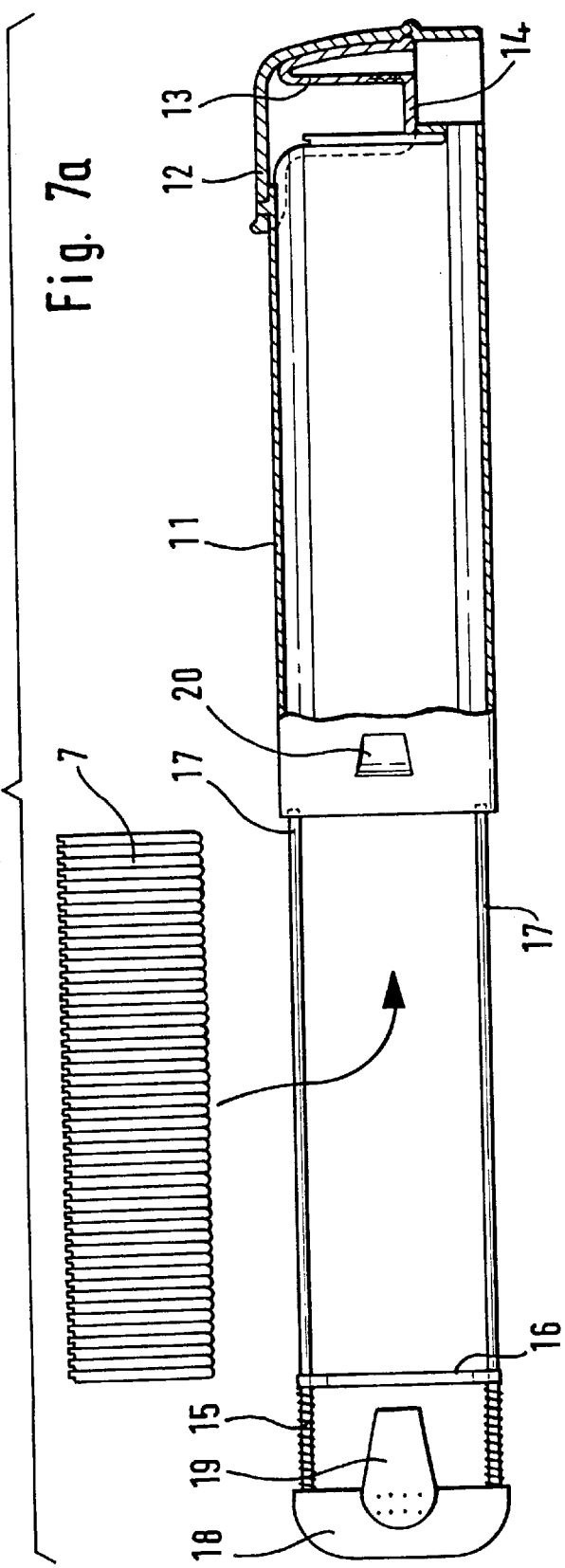
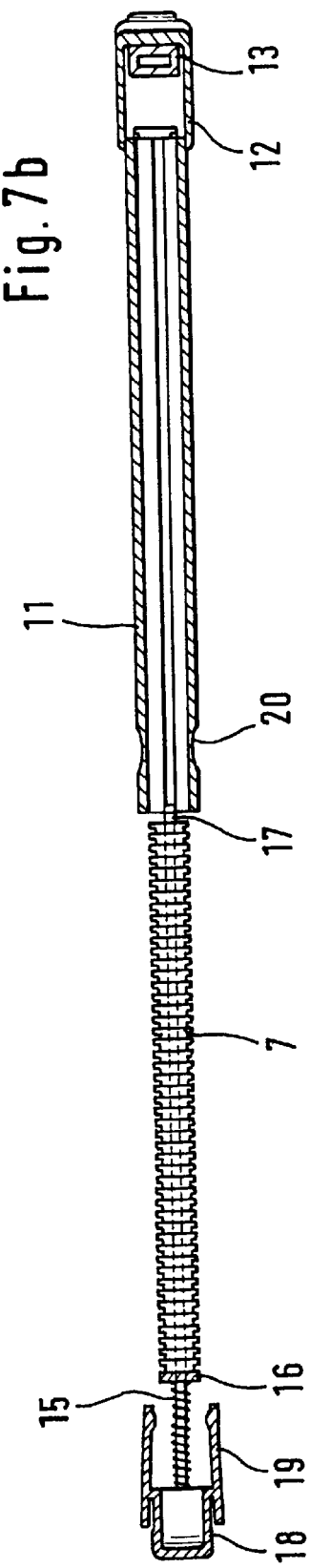

ANALYTICAL SYSTEM FOR SAMPLE LIQUIDS

CROSS-REFERENCES TO RELATED APPLICATIONS

Not Applicable

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The invention concerns a system for the analysis of sample liquids, comprising test elements, a moisture-impermeable, tightly sealable storage container for at least two test elements and a measuring instrument that is independent of a power supply network and can be held with one hand. The invention also concerns a method for the determination of an analyte in a sample liquid.

2. Description of the Related Art

Analytical elements that allow the determination of individual parameters in sample liquids have been known for some time and a great variety of them are commercially available. In particular, systems are available for the fields of medical diagnostics and environmental analysis which can also be operated by persons with little training. Those systems are simple to operate which do not require the use of liquid reagents and in which preparation of the sample material is in general unnecessary or can be accomplished in an uncomplicated manner. A "dry chemistry" was developed for such so-called rapid tests where the water contained in the sample liquid serves alone as the solvent.

For example, systems are commonly used to determine glucose in blood in which the patient applies small amounts of freshly collected blood to a test strip and carries out the measurement using an instrument that can be operated simply, for example a reflection photometer. In analytical systems of the most common prior art, the test elements are present separately outside the measuring instrument and are only inserted into the measuring instrument for the actual measurement process.

Conventional measuring instruments have an opening, for example a slit, in which a test strip can be inserted by hand. Guiding elements ensure that a test strip is inserted in the intended orientation. Constructive features of the instrument must be present to ensure the desired positioning of the test strip. This is usually achieved by a stop which prevents insertion beyond a predetermined target position.

Although recently more and more systems based on electrochemical sensors have been offered for sale, the most common systems use analytical tests which are based on color changes that are exhibited during the course of the detection reaction when analytes to be determined are present. Detection of the color change occurring on the test strip can be carried out by reflection photometry. A transmission measurement is also possible but requires at least partially transparent test strips. The devices that are necessary for the photometry for generating and detecting radiation are in principle known in the prior art.

Test strips of the prior art have a test zone and a holder for this test zone usually in the form of a stiff foil which enables a comfortable and safe handling of the test strip. The test zone itself can be composed of several layers. Layers of fleece materials are for example usual for determining analytes in blood which separate cellular components from serum. In addition, layers are commonly used in which reactions take place or which contribute to the dosing of the sample material. Typical structures of test strips are for example described in the German Patent Applications DE 196 296 56.0 and DE 196 296 57.9 and in EP-B 0 271 854, EP-A-0 487 068, WO 92/17768 and DE-A 195 23049.

Only in a few cases is the analyte detected by reaction of the analyte with a single substance to directly form a dye. Usually, a chain of chemical and/or biochemical reactions occurs which finally lead to an observable change in color. The test zone on which the color reaction can be observed must have a size and shape that ensures a zone of constant size is irradiated or radiated even with the manufacturing tolerances of the measuring instrument and test element.

Test elements known from the prior art essentially have the shape of a flat strip or a flat rectangular plate. Paper and in particular cardboards and plastics are commonly used as materials. The test zone is either applied to the said materials by impregnation of the material with the corresponding reagents or in the form of additional layers.

The storage stability of many test elements is greatly reduced by the influence of moisture, for example, from the ambient air since the test zones often contain sensitive, usually biochemical reagents. For this reason, commercially available test elements are either individually sealed or are provided in large amounts packaged in special containers. Sealing is usually carried out in plastic laminated metal foils, preferably aluminum laminates. This packaging form is used above all for rapid tests that are to be evaluated by an instrument or visually. In order to use a sealed test element, the packaging is torn open manually and the test element is removed. In the case of test strips which have to be used more frequently by the user, for example blood glucose test strips for diabetics, several of them are usually present in re-sealable containers made of moisture-impermeable materials which can also contain desiccants to absorb moisture that has entered.

The measurement process with the said systems for analysis with dry chemistry rapid tests is carried out using an analytical instrument and separate test strips for single use. For this the user of the system manually opens a storage container, removes a test strip and closes the container again in order to protect the remaining test strips in the storage container from moisture. Afterwards, the sample liquid to be analysed is applied to the sample application zone of the test strip. The test strip is inserted into the analytical instrument either directly after sample application or after an incubation period. In more modern systems, the sample application does not take place until the test strip is in the instrument. In both procedures, the test strip is inserted manually into the measuring instrument by the operator. The positioning of the test strip is ensured by constructive measures.

The actual measurement process is usually started by the operator's act of pressing a button. There are also systems in which the measurement process is started automatically when the test strip is inserted into the instrument. After completion of the measurement which the user sees on the instrument display, the analytical process is ended by removing the test strip.

A disadvantage of the described systems for analysing sample liquids is that the operator usually has to carry out several handling steps with the test elements. Since the users of such systems, particularly in the field of medical diagnostics, are often diabetics which have great difficulty in safely handling small test elements, there is a need to construct analytical systems which do not require the handling of individual test elements or reduces this to a minimum.

A further disadvantage of current systems is the manual positioning of the test strips by the operator which does not reliably prevent operating errors. Consequently, attempts are made to provide systems in which the test elements are positioned in such a way that operating errors that are due to improper positioning are reliably avoided.

Since the test strips which are used in the common systems exhibit manufacturing tolerances in their detection characteristics, a correct evaluation requires the transmission of batch-specific characteristic data to the measuring instrument. Nowadays, batch codes are often used for this which are either directly mounted on the test strips and are automatically registered when the strip is inserted into the instrument or they are present on the packaging of the test strips and have to be entered manually by the operator for example by means of a keyboard. Both variants are not an optimal solution. In order to code the individual test strips, the manufacturer must first randomly analyse the functional characteristics before the strips can be provided with a code. Hence, the production process cannot be completed in one step which makes the process complicated and ultimately expensive. If in contrast the package is furnished with the code, the production process can indeed be completed before the coding but errors may occur when the code is transmitted manually from the package to the instrument for example by false or erroneous input by the operator. Therefore, the aim is to optimize the code transmission.

The object of the present invention was to eliminate the disadvantages of the prior art.

This is achieved by the subject matter of the invention as characterized in the patent claims.

SUMMARY OF THE INVENTION

The present invention concerns a system for the analysis of sample liquids, comprising:

a) test elements comprising an edge profile;

b) a moisture-impermeable, tightly sealable storage container for at least two test elements containing a guide element, a spacer between the guide pilot and the first element to be removed, and a transport device for test elements; and c) a measuring instrument that is independent of the power supply network and can be held with one hand containing a guide groove for test elements, an opposite guide groove for the guide element of the test element storage container as well as a holding device for test elements.

The system according to the invention is a measuring instrument with a separate storage container, i.e., a storage container that is not permanently connected to the measuring instrument, i.e., it is removable e.g. in the form of a dispenser package for test elements. The dimensions of the measuring instrument are preferably such that it can be comfortably held by the operator in one hand. For practical reasons, the power supply is independent of the power supply network and preferably uses batteries, accumulators or solar cells. The measuring instrument is equipped with an easily readable display for the measured values preferably in the form of a liquid crystal display (LCD).

The shape of the measuring instrument is essentially a flat, elongate cuboid. The housing of the measuring instrument is typically manufactured from a light and stable material, preferably a light metal or a plastic. Depending on the desired operating convenience, the required switches may be located on the outside of the instrument housing, for example switches to switch the instrument on and off and optionally operating knobs for additional functions such as time display, storage of the measured values etc. In a particularly advantageous embodiment, the instrument has a pressure switch to actuate an ejection mechanism for test elements that are in the instrument. The measurement display which is preferably in the form of a liquid crystal display, and in a particularly preferred embodiment of the invention a guide groove for test elements in which a holding device for test elements is integrated, are located on the front side of the instrument. Opposite the guide groove for test elements and preferably at the rear of the instrument housing, there is a recess which is designed as a guide groove for the guide element of the storage container for test elements. Alternatively, the guide grooves can also be arranged next to one another in which case the front and rear side of the instrument can contain the grooves. In addition, a battery or accumulator drawer for the power supply of the measuring instrument may be provided preferably at the rear. The instrument is preferably automatically switched on, for example by inserting a test strip into the instrument. It can also be switched off automatically for example when the used test strip is removed from the instrument. However, both functions can also be carried out manually for example by operating a switch or button. It is also possible that manual as well as automatic operation is possible or necessary. Functional constructive details of the components of the measuring instrument that are essential for the invention are described below.

The system according to the invention greatly simplifies the removal of the test elements from the package and insertion into the instrument compared to conventional systems. The test element removal is carried out directly with and by the instrument. This means that the test elements no longer have to be inserted by hand by the user. Hence a grip surface on the test element is no longer necessary. Consequently the size of the test elements is no longer determined by handling criteria as was previously the case, but can be reduced to the minimum possible size which is functionally determined. This saves material in the manufacture of the test elements. The small size also has a positive effect in that the is package size is smaller for the same number of test elements.

The storage container is designed for at least two test elements. Practically the total number of test elements to be stored is between 10 and 100, preferably 50. The storage container is preferably designed as a dispenser package in which a mechanism ensures that always one test element is ready for removal at a special removal position. The dispenser package is preferably manufactured from a material that is as impermeable to moisture as possible and in particular from an essentially moisture-impermeable plastic. In this case moisture-impermeable means that water as well as liquid and vapour cannot penetrate through the material of the dispenser package or is at least substantially prevented from passing through. The dispenser package is preferably equipped with a flap and can be opened or closed with this. When the flap is closed, the dispenser package is for example sealed airtight by packing washers or O-rings to substantially reduce penetration of moisture. A desiccant is preferably located inside the storage container to absorb moisture which can penetrate into the storage container when it is for example opened and hence to protect the test elements from moisture.

In a preferred embodiment the guide element is located under the flap in the closed state which becomes accessible when the flap is opened and over which the instrument is slid when test elements are removed. A test element with a, preferably step-like, edge profile is located in the removal position at a pre-determined distance from the guide element defined by a spacer. All other test elements are stacked next to or behind one another in the dispenser package preferably pair-wise with their surfaces touching and, in a particularly preferred embodiment, bonded together at a small contact site which can be readily detached again in order to ensure a constant orientation relative to one another especially when the storage container is loaded with test elements. Once a test element has been removed, it is automatically replaced by the respective next test element by a transport device, preferably by a spring mechanism. The inner walls of the storage container are preferably shaped so that they serve as a guide for the test element transport.

The spring mechanism preferably essentially corresponds to the transport mechanism that is known from rifle or pistol magazines or from staplers. It typically comprises a spiral spring and a plate that is preferably guided by guide rails or guide rods or wall profiles and that transfers the spring pressure onto the test elements and thus ensures that the test elements are directed from the inside of the container to the removal position.

The test element storage container is preferably designed as a flat, bar-shaped cuboid which has a flap at one end. Under the flap there is especially preferably a test element in the removal position, a guide element as well as a spacer which spaces the guide element and test element in the removal position.

In a particularly preferred embodiment, the test element storage container also comprises a tightly-sealable opening for filling the container with test elements in addition to the removal opening which is for example provided with a flap. The test element storage container is preferably capable of multiple use which is why the test elements can be simply refilled by the operator as required. For example, one of the boundary surfaces of the storage container can be reversibly removed so that the test elements to be refilled can be inserted individually or preferably together, for example linked by a detachable adhesive, into the container. Particularly preferably, the filling process reactivates the transport mechanism e.g. by tensioning a spring.

The storage container is preferably loaded with test elements starting at the bottom of the container. In the case of essentially cuboid containers the bottom is that boundary surface of the storage container which is essentially perpendicular to the transport direction of the test elements in the container. In a preferred embodiment the bottom can be bound firmly and tightly to the body of the container by means of a locking mechanism. The locking mechanism is released in order to insert new test elements into the storage container and the bottom to which preferably the transport mechanism for the test elements for example a spring or one or several guide rails or rods is attached, is removed from the container. In this case, the bottom can be linked via a guide to the container like a drawer or be completely detachable. If the bottom is essentially completely detachable, the test elements to be refilled can be directly filled into the inside of the test element storage container. Otherwise, the test elements can be placed in or on the guide with which the bottom is linked to the container like a drawer and thus be transported into the inside of the container. The transport mechanism is reactivated for example by tensioning the spring(s) when the test elements are inserted similar to the loading of staplers with staples. The test elements to be refilled can for example be provided in a transport package, for example a tightly-sealable can, tube, welded foil or a blister package from which they have to be removed to fill the storage container.

As an alternative to the cuboid shape the storage container can also be in the shape of a flat plate, for example, a quadratic or round plate which has a recess at the edge in which the measuring instrument can be inserted to remove the test elements.

The guide element of the storage container in conjunction with the corresponding guide groove of the measuring instrument serves to unequivocally orient the measuring instrument relative to the storage container and thus also relative to the test elements arranged therein during the removal process. A false orientation is excluded by appropriate dimensions of the guide groove and guide element. Thus, the test elements cannot be inserted in a false alignment.

The guide element is preferably designed as a peg which is especially preferably located near the edge of the storage container.

In a preferred embodiment, the guide pilot is essentially cuboid-shaped in which one base surface of the cuboid is permanently bound to the storage container. The shape and size of the corresponding guide groove in the measuring instrument matches the guide pilot and is also essentially a cuboid depression in the housing of the measuring instrument. When the test element storage container and measuring instrument are joined together in order to remove a test element from the storage container with the measuring instrument, the guide pilot slides in the guide groove. This determines the path of the measuring instrument relative to the storage container which concomitantly guarantees an unequivocal orientation of the measuring instrument relative to the test elements contained in the storage container.

The guide element and guide groove are preferably matched together such that the test element storage container and the measuring instrument can be joined together without applying a large force. For this purpose, the guide groove is kept slightly larger than the guide element without the two components having too much play. The guide groove is preferably on the rear side i.e. arranged on the opposite side of the measuring instrument to the measurement display and has a slightly conical or funnel shaped opening into which the guide element which is preferably also conical can easily be inserted. A rounding of the edges of the guide element and groove which is particularly preferred also facilitates the joining of the guide element and groove.

In a preferred embodiment, a batch-specific coding is located in or on the guide element preferably on the side facing the instrument. A corresponding code reading device is located in the corresponding guide groove of the measuring instrument which automatically reads the code when the guide element is pushed out or in and is available to the measuring instrument for evaluation. Optical or electromagnetic codes come into particular consideration as the coding and preferably bar codes, magnetic strip codes or general codes which are stored in a so-called "read-only memory" (ROM). The measuring instrument in each case contains corresponding devices which are suitable for reading the code. Numerous coding and reading methods are known to persons skilled in the art and do not need to be elucidated in more detail here.

When the strip is removed, the batch-specific code of the test elements is automatically transmitted to the instrument. This ensures that the batch identification of the respective test element being examined is in all cases transmitted without mistake. The instrument is preferably already switched on before removing the test element so that the code is already read during removal of the test element when the instrument is joined to the storage package. Alternatively, the code can be read when the instrument and dispenser package are separated for example when the instrument is automatically switched on by inserting the test element into the instrument.

In a preferred embodiment, a guide groove for test elements is located at the lower end of the instrument on the front side. In this connection, the front side of the instrument is the side on which the data display for example an LCD display is located. In contrast to the upper end of the instrument, the lower end of the instrument is that end which is at the greatest distance from the data display. The profile along the edge of these test elements is preferably such that part of the edge forms a spring which fits into the corresponding guide groove of the instrument. A guide groove is preferably present at the opposite lower end of the instrument, i.e. for example on the rear side, into which the guide element of the dispenser package fits. The two guide grooves preferably have different dimensions i.e. they have a different size and/or different shape to exclude a mistaken erroneous insertion of the instrument. This also ensures that the test elements are automatically correctly inserted into the instrument.

When a test element is withdrawn, the lower end of the instrument is pushed, preferably from above, between the guide element and test element at right angles to the package until the profiled test element slides into the guide groove provided. The test element is held in an optimal position in the measuring instrument by a holding device. The operator knows by touch and sound when the final position is reached. Finding the correct position without mistakes is ensured by the rearward guide groove of the instrument in conjunction with the guide element of the storage container. When the instrument is pulled out, the test strip is held by the holding device in the locked position. A locking mechanism is preferably used as a holding device which engages the test element in a recess, for example, a hole. For example, the folding device can be composed of a spring supported ball or a pre-tensioned plastic hook or one of the mechanisms mentioned in EP-A 0 618 443. In a preferred embodiment, an ejection device is provided in the measuring instrument to remove the test elements after completion of the analysis so that the operator of the system does not have to touch the test element with his hands after the measurement which ensures a hygienic disposal of used test elements. For example, a push rod operated by a pressure button can serve as the ejection mechanism. By pressing the pressure knob the test element is pushed out of the instrument in the direction of pressure against the resistance of the holding mechanism and is finally ejected.

Since the test elements of the system according to the invention can be directly withdrawn from the storage container with the aid of the measuring instrument, the sample application takes place on a test element which is in the measuring instrument. In order to largely avoid contamination of the measuring instrument, for example by blood, it is practical to dimension the test elements such that after insertion into the measuring instrument they protrude slightly, preferably 5 to 15 mm, from the measuring instrument. The sample is preferably applied to the end of the test element which protrudes from the measuring instrument. Since for calorimetric tests it is practical to have the detection unit of the measuring instrument in the inside of the instrument, it is preferable that the test zone of the test element comes to rest at least partially in the interior of the instrument to enable a detection at all. This requires that the sample be transported by suitable means contained within the test element from the sample application site to the detection site. Particularly preferred means for transporting the sample from the sample application site to the detection site is a capillary active channel as known for example from EP-A 0 487 068, EP-A-0 215 419 or DE-A 31 51 291. However, other means for transporting the sample are possible, for example, fleeces with a wicking effect or similar means.

In the case of electrochemical detection methods, for example with amperometric or potentiometric sensors and biosensors, the sample liquid can be applied directly to the detection site located outside the measuring instrument. In order to detect the electrical detection signal, this is led into the measuring instrument with the aid of suitable conducting elements for example printed or etched conducting paths where it is optionally amplified, analysed and displayed.

A further subject matter of the invention is a method for the determination of an analyte in a sample liquid with the aid of a system according to the invention. The method is characterized in that firstly a test element is withdrawn from the opened storage container with the aid of the measuring instrument. A sample liquid is applied to the sample application zone on the test element located in the instrument which independently reaches the detection zone where it undergoes a characteristic detectable reaction with the components of the test zone for example with a change of color or accompanied by an electrochemically observable conversion. The result of the reaction is detected with the aid of the instrument and displayed. Finally, after the analysis, the used test element is removed from the measuring instrument optionally with the aid of the ejection device.

BRIEF DESCRIPTION OF THE DRAWINGS

The invention is illustrated in FIGS. 1 to 7.

FIG. 1 shows a particularly preferred embodiment of the measuring instrument of the system according to the invention in different views as follows: (a) front view, (b) rear view, (c) side view, and (d) a view from below.

FIG. 2 shows a particularly preferred embodiment of the test element with edge profile of the system according to the invention in different views (a) from above, (b) from below, (c) side view, and (d) front view of the end surface.

FIG. 3 is a particularly preferred embodiment of the test element storage container of the system according to the invention in a closed (a) and opened (b) state.

FIG. 4 shows schematically how a test element is withdrawn by the measuring instrument from the storage container with the aid of the system according to the invention.

FIG. 6 shows a longitudinal section from the side (a) and from above (b) as well as a cross-section (c) through a further particularly preferred embodiment of the test element storage container of the system according to the invention in a closed state.

FIG. 7 shows a longitudinal section from the side (a) and from above (b) through the particularly preferred embodiment of the test element storage container of the system according to the invention according to FIG. 6 in which the bottom is open to load test elements.

DETAILED DESCRIPTION OF THE INVENTION

Figure 5:
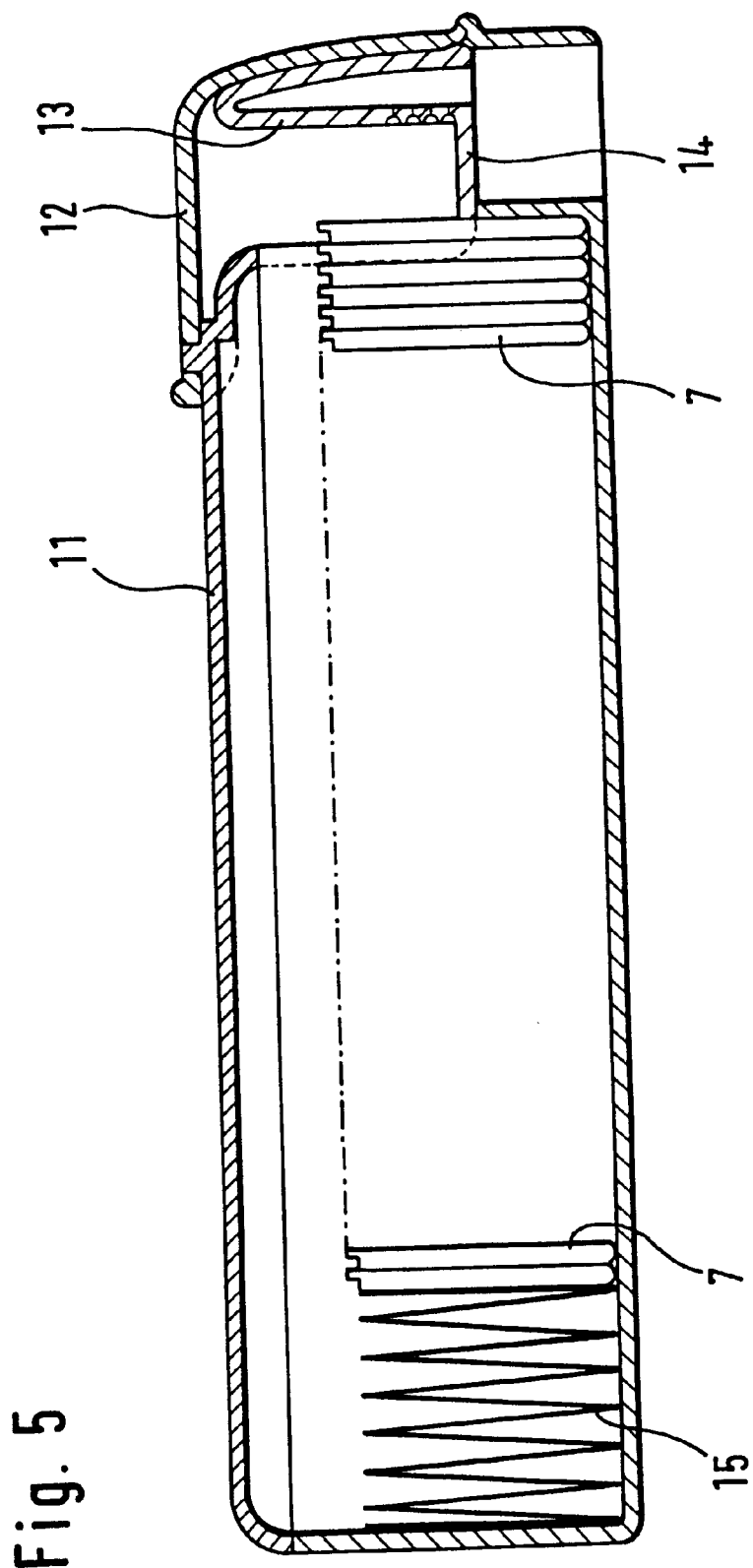
FIG. 5 shows a longitudinal section through a particularly preferred embodiment of the test element storage container of the system according to the invention.

The numbers in the figures denote:

1 measuring instrument housing 2 display
3 guide groove for test element
4 holding device
5 pressure switch for the ejection device
6 guide groove for the guide pilot with a code reading device
7,7' test element with edge profile
8 recess
9 test zone (detection site)
10 sample application site
11 housing of the storage container
12 flap
13 guide pilot with coding
14 spacer
15 spring
16 plate
17 guide rod
18 removable bottom
19 click closure
20 recess for the click closure measuring instrument that is part of the system according to the invention is shown in FIG. 1. On the front side of the instrument (FIG. 1a), there is a guide groove (3) for test elements integrated into the housing of the measuring instrument (1) in addition to an easy to read display (2). FIG. 1d shows that the guide groove (3) has a profile which is complementary to the profile of the test elements. The holding device (4) for test elements is located in the area of the guide groove (3). The guide groove (6) for the guide pilot of the test element storage container is located on the rear side of the measuring instrument (FIG. 1b). As shown especially in FIG. 1d the guide groove (3) for test elements is exactly opposite the guide groove (6) for the guide pilot. The two guide grooves (3,6) differ in shape and dimensions in order to ensure a safe error-free handling of the system.

The guide groove (6) comprises a device for automatically registering the coding which is located on or in the guide pilot of the test element storage container. This can, for example, be a bar code reading device.

The measuring instrument of the system according to the invention is equipped with an ejection device for used test elements. This is operated by a pressure switch (5). This allows used test elements to be detached and ejected from the holding device (4).

Test element (7) shown in FIG. 2a to 2d contains an edge profile (FIG. 2d) which ensures that the test element (7) is correctly oriented in the measuring instrument and, in conjunction with the recess (8) in the holding device (4) of the measuring instrument as well as its guide groove (3), holds the test element (7) firmly in the measuring instrument during the measurement.

The test element (7) contains means such as a capillary active channel, which ensure that the sample is transported from the sample application site (10) to the detection site (9). In the case of test elements that are to be evaluated optically, the detection site (9) is visible on the rear side of the test element facing the instrument (FIG. 2b). In the case of electrochemical sensors, the sample application site (10) can be identical to the detection site (9).

FIG. 3 shows a diagram of the test element storage container. In the closed state (FIG. 3a), only the housing of the storage container (11) and the closable flap (12) is visible. In the open state (FIG. 3b), the flap (12) is folded back. As a result, the first test element (7) and the guide pilot with the coding (13) are exposed and a spacer (14) creates a gap between them into which the measuring instrument can be inserted to withdraw the test elements (7).

In addition to the visible test element (7) which is in the withdrawal position, the storage container also contains further test elements lined up side by side which are successively transported to the withdrawal position by a transport device, e.g., a spring mechanism.

The withdrawal process for test elements (7) from the storage container with the aid of the measuring instrument is shown in FIG. 4 on the basis of three different positions (FIG. 4a to c).

FIG. 4a shows how the measuring instrument is guided onto the opened storage container in correct mutual orientation. The guide groove (3) for test elements (7) faces the test element and the guide groove (6) for the guide pilot (13) faces the guide pilot (13).

The measuring instrument is lowered onto the storage container until the position shown in FIG. 4b is reached. As the test element (7) is lowered, it is positioned and locked into position and simultaneously the instrument is automatically switched on.

When the measuring instrument is removed from the storage container, the code on the guide pilot (13) is read by the code reading device in the corresponding guide groove (6). In this process, the test element (7) is withdrawn from the storage container and is available for measurement (FIG. 4c).

Withdrawal of the test element (7) from the storage container leaves the removal position vacant. This is automatically occupied by the following test element (7') which is conveyed by the transport mechanism.

The sample application site (10) of the test element (7) located in the measuring instrument is contacted with the sample. The sample is for example transported by capillary forces to the detection site (9) where a measurement takes place after or already during the detection reaction, for example a reflection-photometric observation of a color change related to the type and amount of the analyte present in the sample liquid. The direct measurement result is converted by the measuring instrument into a display value by means of suitable algorithms and is displayed and optionally stored After the measurement, the test element (7) is removed from the instrument by operating the pressure switch (5) of the ejection device. Operation of the pressure switch (5) of the ejection device can simultaneously switch off the instrument.

A particularly preferred embodiment of the test element storage container of the system according to the invention is shown in FIG. 5 in longitudinal section from the side. The sectional view shows the transport mechanism which moves the test elements (7) into the withdrawal position. The transport mechanism of the embodiment shown here is essentially composed of a spring (15) which presses directly against the nearest test element (7). This presses the test elements (7) against the spacer (14) which spatially separates the test element located in the withdrawal position under the flap (12) from the guide pilot (13). In this embodiment, the test elements (7) are essentially guided by the housing of the storage container (11) which has a corresponding geometric shape.

FIG. 6 shows a longitudinal section from the side (a) and from above (b) as well as a crosssection (c) through a particularly preferred embodiment of the test element storage container of the system according to the invention in a closed state. In this embodiment, the transport mechanism comprises two springs (15) which press on a plate (16) which in turn acts on the test elements (7). In this case, the guidance is achieved by two guide rods (17) in combination with the geometry of the storage housing (11) which can be seen in particular from the cross-section (c).

The variant shown in FIG. 6 has a removable bottom (18) which can be removed from the storage container housing (11) after releasing a click closure (19) for the purpose of refilling test elements (7). FIG. 7 shows a longitudinal section from the side (a) and from above (b) through the particularly preferred embodiment of the test element storage container of the system according to the invention according to FIG. 6 in the opened state for loading with test elements (7). The test elements (7) are glued together by means of a readily detachable adhesive via a small contact site to enable a simple filling of the test element storage container.

For the purposes of filling, the bottom (18) is removed after detaching the click closure (19). The guide rods (17) hold the bottom (18) in a geometrically defined position relative to the container housing (11). The test elements (7) are inserted directly into the container (arrow) which is subsequently sealed again by the bottom (18). For this purpose, the click closures (19) lock into the recesses (20) provided in the housing (11). The housing is sealed as in the case of the removal flap (12) by packing washers or O-rings. When it is closed, the springs (15) are automatically tensioned again and the transport mechanism is reactivated.

What is claimed is:

1. A system for the analysis of sample liquids, comprising:
    a) test elements comprising an edge profile;
    b) a moisture-impermeable, tightly sealable storage container for at least two test elements comprising a guide element, a spacer between the guide element and the first test element to be withdrawn from said storage container, and a transport device for transporting test elements; and
    c) a measuring instrument that is independent of a power supply network and can be held with one hand, the instrument comprising a guide groove for test elements, an opposing guide groove for the guide element of the storage container, and a holding device for test elements.

2. The system of claim 1, wherein the measuring instrument comprises an ejection device for test elements.

3. The system of claim 1, wherein the guide element of the storage container comprises a coding.

4. The system of claim 3, wherein the measuring instrument comprises a device for automatically registering the coding that is located on or in the guide element of the storage container.

5. The system of claim 1, wherein the test elements comprise a means to transport the sample from a sample application site to a sample detection site.

6. The system of claim 5, wherein the transport means comprises a capillary active channel.

7. The system of claim 1, wherein the test elements comprise a recess so that they can be easily held in the measuring instrument.

8. The system of claim 1, wherein the storage container comprises a spring mechanism for use as a transport device for test elements.

9. The system of claim 1, wherein the storage container comprises a removable bottom.

10. The system of claim 3, wherein the guide element of the storage container comprises a bar code or a ROM component as the coding.

11. The system of claim 4, wherein the guide element of the storage container comprises a bar code or a ROM component as the coding.

12. The system of claim 1, wherein the holding device of the measuring instrument comprises a locking mechanism.

13. The system of claim 4, wherein the device for automatically registering the coding comprises a bar code or ROM reading device.

14. The system of claim 1, wherein the guide groove for test elements and the guide groove for the guide element of the storage container have different dimensions in the measuring instrument.

15. A method for the determination of an analyte in a sample liquid with the aid of a measuring instrument, comprising:
    a) removing a test element from an open storage container with the aid of the measuring instrument;
    b) contacting a sample application zone of the test element located in the instrument with a sample liquid which is automatically transported into a detection zone so that the sample liquid there reacts characteristically and detectably with at least one reagent component of the detection zone, therby producing a reaction result;
    c) detecting and displaying the reaction result with the aid of the measuring instrument; and
    d) removing the test element from the measuring instrument after the analysis.

* * * * *